United States Patent
Davey

(10) Patent No.: US 10,406,336 B2
(45) Date of Patent: Sep. 10, 2019

(54) ADJUSTABLE RATE DRUG DELIVERY IMPLANTABLE DEVICE

(71) Applicant: Neil S. Davey, Gaithersburg, MD (US)

(72) Inventor: Neil S. Davey, Gaithersburg, MD (US)

(*) Notice: Subject to any disclaimer, the term of this patent is extended or adjusted under 35 U.S.C. 154(b) by 1 day.

(21) Appl. No.: 15/661,575

(22) Filed: Jul. 27, 2017

(65) Prior Publication Data
US 2018/0036522 A1 Feb. 8, 2018

Related U.S. Application Data

(60) Provisional application No. 62/370,675, filed on Aug. 3, 2016.

(51) Int. Cl.
*A61M 31/00* (2006.01)
*A61K 9/00* (2006.01)
(Continued)

(52) U.S. Cl.
CPC ......... *A61M 31/002* (2013.01); *A61F 5/0013* (2013.01); *A61K 9/0097* (2013.01); *A61K 31/565* (2013.01); *A61K 31/57* (2013.01); *A61K 38/26* (2013.01); *A61K 38/28* (2013.01); *A61M 5/14276* (2013.01); *A61M 5/14526* (2013.01); *A61K 9/0004* (2013.01); *A61K 9/0024* (2013.01); *A61M 2005/14513* (2013.01); *A61M 2205/33* (2013.01); *A61M 2205/8206* (2013.01); *A61M 2250/00* (2013.01)

(58) Field of Classification Search
None
See application file for complete search history.

(56) References Cited

U.S. PATENT DOCUMENTS

| 5,514,378 A | 5/1996 | Mikos |
| 5,797,898 A | 8/1998 | Santini, Jr. |

(Continued)

FOREIGN PATENT DOCUMENTS

| WO | WO 01/45675 A8 | 6/2001 |
| WO | WO 2005/079703 A1 | 9/2005 |

(Continued)

OTHER PUBLICATIONS

European Search Report dated Apr. 12, 2018 for EP Application No. 17184728.8, filed Aug. 3, 2017, 11 pages.

*Primary Examiner* — Nathan R Price
*Assistant Examiner* — Mark Alan Igel
(74) *Attorney, Agent, or Firm* — Raju Dave; Dave Law Group, LLC

(57) ABSTRACT

Embodiments herein relate to an implantable device comprising a casing, a semi-permeable membrane plug at or near a first end of the casing, a piston, beads, and an opening for release of the beads from the implantable device within a body of a human or an animal; wherein the implantable device is configured to be implanted within the body of the human or the animal during delivery of the beads into the body of the human or the animal; wherein the beads comprise a core and a shell with the core being enclosed by the shell and the beads contain a drug; and wherein the implantable device is configured to produce a desired flow rate of elution of the drug from the implantable device when the implantable device is implanted within the body of the human or the animal.

22 Claims, 3 Drawing Sheets

(51) Int. Cl.
  *A61K 38/26*   (2006.01)
  *A61K 38/28*   (2006.01)
  *A61M 5/145*   (2006.01)
  *A61F 5/00*    (2006.01)
  *A61K 31/565*  (2006.01)
  *A61K 31/57*   (2006.01)
  *A61M 5/142*   (2006.01)

(56) References Cited

U.S. PATENT DOCUMENTS

| | | | |
|---|---|---|---|
| 5,997,527 | A | 12/1999 | Gumucio |
| 6,123,861 | A | 9/2000 | Santini, Jr. |
| 6,132,420 | A | 10/2000 | Dionne |
| 6,190,350 | B1 | 2/2001 | Davis |
| 6,287,295 | B1 | 9/2001 | Chen |
| 6,491,666 | B1 | 12/2002 | Santini, Jr. |
| 6,508,808 | B1 | 1/2003 | Pan |
| 6,524,305 | B1 | 2/2003 | Peterson |
| 6,537,256 | B2 | 3/2003 | Santini, Jr. |
| 6,544,252 | B1 | 4/2003 | Theeuwes |
| 6,808,522 | B2 | 10/2004 | Richards |
| 6,858,220 | B2 | 2/2005 | Greenberg |
| 6,872,201 | B2 | 3/2005 | Theeuwes |
| 6,939,556 | B2 | 9/2005 | Lautenbach |
| 6,976,982 | B2 | 12/2005 | Santini, Jr. |
| 7,014,636 | B2 | 3/2006 | Gilbert |
| 7,070,590 | B1 | 7/2006 | Santini, Jr. |
| 7,070,592 | B2 | 7/2006 | Santini, Jr. |
| 7,226,442 | B2 | 6/2007 | Sheppard |
| 7,354,597 | B2 | 4/2008 | Johnson |
| 7,560,036 | B2 | 7/2009 | Golubovic-Liakopoulos |
| 7,655,257 | B2 | 2/2010 | Peery |
| 7,776,024 | B2 | 8/2010 | Santini, Jr. |
| 7,776,927 | B2 | 8/2010 | Chu |
| 7,790,286 | B2 | 9/2010 | Zhang |
| 7,879,019 | B2 | 2/2011 | Santini, Jr. |
| 7,879,028 | B2 | 2/2011 | Alessi |
| 7,892,221 | B2 | 2/2011 | Santini, Jr. |
| 7,901,397 | B2 | 3/2011 | Santini, Jr. |
| 7,918,842 | B2 | 4/2011 | Santini, Jr. |
| 8,021,357 | B2 * | 9/2011 | Tanaka .............. A61M 5/14248 604/890.1 |
| 8,308,707 | B2 | 11/2012 | Santini, Jr. |
| 8,343,140 | B2 | 1/2013 | Alessi |
| 8,367,095 | B2 | 2/2013 | Lautenbach |
| 8,403,907 | B2 | 3/2013 | Sheppard, Jr. |
| 8,535,701 | B2 | 9/2013 | Peery |
| 8,801,700 | B2 | 8/2014 | Alessi et al. |
| 8,801,801 | B2 | 8/2014 | Datta |
| 8,821,474 | B2 * | 9/2014 | Shekalim .......... A61M 5/14248 604/502 |
| 2006/0127925 | A1 * | 6/2006 | Stayton ............. C12N 15/1006 435/6.12 |
| 2007/0141102 | A1 | 6/2007 | De Graaff |
| 2007/0184082 | A1 * | 8/2007 | Magdassi ............ A61K 9/0024 424/422 |
| 2007/0190145 | A1 * | 8/2007 | Venkatesh ........... A61K 9/2077 424/470 |
| 2007/0287984 | A1 * | 12/2007 | Lobl ................... A61M 5/1409 604/416 |
| 2008/0112892 | A1 | 5/2008 | Veenstra |
| 2008/0187579 | A1 | 8/2008 | Bhat |
| 2009/0081278 | A1 | 3/2009 | De Graaff |
| 2010/0104619 | A1 | 4/2010 | De Graaff |
| 2010/0129425 | A1 | 5/2010 | De Graaff |
| 2010/0129459 | A1 | 5/2010 | Kwak |
| 2010/0203104 | A1 | 8/2010 | De Graaff |
| 2011/0076317 | A1 | 3/2011 | Alessi et al. |
| 2012/0052108 | A1 | 3/2012 | De Graaff |
| 2012/0058171 | A1 | 3/2012 | De Graaff |
| 2012/0059349 | A1 * | 3/2012 | Kuo .................... A61M 5/1407 604/500 |
| 2012/0141589 | A1 | 6/2012 | Fan |
| 2012/0222748 | A1 * | 9/2012 | Weitz ................... B01F 3/0807 137/1 |
| 2013/0030417 | A1 | 1/2013 | Alessi |
| 2013/0035574 | A1 | 2/2013 | Anand |
| 2013/0035660 | A1 | 2/2013 | Anand |
| 2013/0041353 | A1 * | 2/2013 | Shin .................. A61M 5/14248 604/892.1 |
| 2013/0078286 | A1 | 3/2013 | Groenewegen et al. |
| 2013/0115265 | A1 | 5/2013 | Groenewegen et al. |
| 2013/0202657 | A1 | 8/2013 | Ladavac |
| 2013/0280334 | A1 | 10/2013 | Karp |
| 2014/0056962 | A1 | 2/2014 | De Graaff |
| 2014/0142556 | A1 | 5/2014 | Kuo et al. |
| 2015/0225438 | A1 * | 8/2015 | Johnson ................ A61K 47/22 514/188 |
| 2016/0129111 | A1 | 5/2016 | Ghandehari |
| 2016/0263221 | A1 | 9/2016 | Kordas |
| 2017/0020402 | A1 | 1/2017 | Rogers |
| 2017/0065721 | A1 | 3/2017 | Petros |
| 2017/0073311 | A1 | 3/2017 | Johnson |
| 2017/0119785 | A1 | 5/2017 | Rajagopalan |
| 2017/0135953 | A1 | 5/2017 | Kassab |
| 2017/0165201 | A1 | 6/2017 | Anselmo |

FOREIGN PATENT DOCUMENTS

| | | | | |
|---|---|---|---|---|
| WO | WO 2007/090082 | A3 | 8/2007 | |
| WO | WO 2015074762 | A1 * | 5/2015 | ............ A61K 9/0009 |
| WO | WO-2015074762 | A1 * | 5/2015 | ............ A61K 9/0009 |

* cited by examiner

ADJUSTABLE RATE DRUG DELIVERY IMPLANTABLE DEVICE

RELATED APPLICATIONS

The present application claims priority to U.S. Provisional Application 62/370,675, entitled, "Controlled Drug Delivery Implant," filed on Aug. 3, 2016, which is incorporated herein by reference in its entirety. The present invention is related U.S. Patent Publications: (1) US 20140056962 entitled "DRUG DELIVERY SYSTEM;" (2) US 20130115265 entitled "DRUG DELIVERY SYSTEM;" (3) US 20130078286 entitled "DRUG DELIVERY SYSTEM;" (4) US 20120058171 entitled "ZOO-TECHNICAL IMPLANT;" (5) US 20120052108 entitled "MACROCYCLIC LACTONE DRUG DELIVERY SYSTEM;" (6) US 20100203104 entitled "DELIVERY SYSTEM FOR RISPERIDONE;" (7) US 20100129425 entitled "VAGINAL DELIVERY SYSTEM FOR MIRTAZAPINE," (8) US 20100104619 entitled "DELIVERY SYSTEM FOR A NON-STEROIDAL NON-IONIZED HYDROPHILIC DRUG;" (9) US 20090081278 entitled "Drug Delivery System;" (10) US 20080112892 entitled "X-Ray Visible Implant;" (11) US 20070141102 entitled "Drug delivery system based on polyethylene vinyl acetate copolymers;" (12) US 20060280771 entitled "Drug delivery system;" (13) US 20130280334 entitled "Nanostructured Gels Capable of Controlled Release of Encapsulated Agents;" (14) US 20100129459 entitled "Biodegradable microsphere composition suitable for the controlled release of glucose controlling peptide and formulation thereof," (15) U.S. application Ser. No. 15/011,181, entitled "FULLY OR PARTIALLY DEVICE FOR CONTROLLED DRUG DELIVERY." All U.S. Patents and U.S. Patent Publications referred above and in the application are incorporated, in relevant parts for the purposes of written description, herein by reference in their entirety.

FIELD OF THE INVENTION

The present invention is directed to an adjustable rate drug delivery implant device wherein the flow rate of elution (i.e., release) of the drug from the device can be maintained substantially constant, increased or decreased with time, or even stopped momentarily.

BACKGROUND OF THE INVENTION

Though thousands of effective biopharmaceuticals exist for a wide array of medical/clinical indications, adherence to drug administration remains a severe problem in fully treating these diseases. Given the difficulties in taking a medication every day, or numerous times throughout the day, and the complexities in properly delivering a drug into the body, a small implantable device would be a convenient solution for a large number of patient populations. Such an implantable device would safely allow for the controlled release of a substance into the body, and this drug delivery platform could be used universally for a variety of conditions.

An important limitation in many existing drug delivery implants is that their drug release profiles are not well-controlled. Though it may be required in certain cases, most drug release profiles in an implantable device are undesirable as the drug concentration decreases as a function of time as the drug runs out. The present invention overcomes these limitations and furthermore provides many other added benefits such as targeted delivery of the drug to a target (e.g., tissue or organ) in the body.

SUMMARY OF THE INVENTION

An embodiment relates to an implantable device comprising a pump comprising a casing, a semi-permeable membrane plug at or near a first end of the casing, a piston, beads, and an opening for release of the beads from the implantable device within a body of a human or an animal; wherein the implantable device is configured to be implanted within the body of the human or the animal during delivery of the beads into the body of the human or the animal; wherein the beads comprise a core and a shell with the core being enclosed by the shell and the beads contain a drug; and wherein the pump is configured to produce a desired flow rate of elution of the drug from the implantable device when the implantable device is implanted within the body of the human or the animal.

Preferably, the drug and/or the beads comprise a targeting material or targeting molecule that binds to a certain organ, tissue, object or a specific site within the body of the human or the animal.

Preferably, the shell comprises a stimuli-responsive polymer, more preferably a stimuli-responsive biodegradable polymer, configured to break the shell, before or after implanting or attaching the implantable device in or on a body of a human or an animal, when the beads are exposed to an external stimulus.

Preferably, the shell comprises a first material and a second material; wherein the first material comprises a metal-containing material or a first biodegradable material; wherein the second material comprises a second biodegradable material; wherein the first material is distributed in the second material; wherein the first material is configured to create pores in the second material; wherein the pores allow the drug to flow from within the beads to outside the beads.

Preferably, the metal-containing material is configured to form pores in the shell, before or after implanting or attaching the implantable device in or on a body of a human or an animal, when the beads are exposed to an external stimulus.

Preferably, the metal-containing material comprises metallic particles.

Preferably, the metallic particles comprise iron-containing or manganese-containing particles, or an iron-containing or manganese-containing polymer.

Preferably, the first and second materials comprise polymers.

Preferably, the first material comprises poly lactic acid (PLA) or an iron-containing polymer and the second biodegradable material comprises poly ε-caprolactone (PCL).

Preferably, the core comprises the drug and a polymer. Preferably, the core comprises an emulsion of the drug and the polymer.

Preferably, the desired flow rate of elution of the drug is substantially constant.

Preferably, the desired flow rate of elution of the drug is substantially constant for a first period of time and substantially zero for a second period of time, or vice-versa, or any combinations thereof.

Preferably, the desired flow rate of elution of the drug is increasing or decreasing with time, or any combinations thereof.

The implantable device could further comprise a sensor configured to monitor the concentration of the drug in the body of the human or the animal.

The implantable device could further comprise a side wall at or near a second end of the casing, wherein the casing is substantially tubular having at least the first end of the casing and the second end of the casing, and the second end of the casing is opposite the first end of the casing.

The implantable device could further comprise a sonicator or a plate with holes therein, wherein the sonicator or the plate is located between the piston and the side wall.

The implantable device could further comprise a first chamber between the semi-permeable plug and the piston, a second chamber between the piston and the sonicator or the plate, and a third chamber between the second chamber and the side wall, wherein the first chamber comprises a salt solution, the second chamber comprises the beads, and the third chamber comprises a foam.

Preferably, the sonicator is configured to sonicate and increase porosity of the foam.

Preferably, some or all of the holes in the plate are filled with a phase-change material.

Preferably, the side wall contains the sensor.

Another embodiment relates to an implantable device comprising a pump that is configured to produce a flow rate of elution of a drug from the implantable device to be maintained substantially constant, increased or decreased with time, or even stopped momentarily; beads comprising a core and a shell, the core being enclosed by the shell, the core comprising the drug, and the shell comprising a first material and a second material; wherein the first material is distributed in the second material; wherein the first material is configured to create pores in the shell; wherein the pores allow the drug to be released from the core to the exterior of the shell through the pores.

Preferably, the first material comprises a metal-containing material that forms the pores in the shell or a first biodegradable material that degrades over time, and the second material comprises a second biodegradable material.

Preferably, the metal-containing material is configured to form pores in the shell, before or after implanting or attaching the implantable device in or on a body of a human or an animal, when the shell is exposed to an external stimulus.

DETAILED DESCRIPTION OF THE INVENTION

Figure 1:
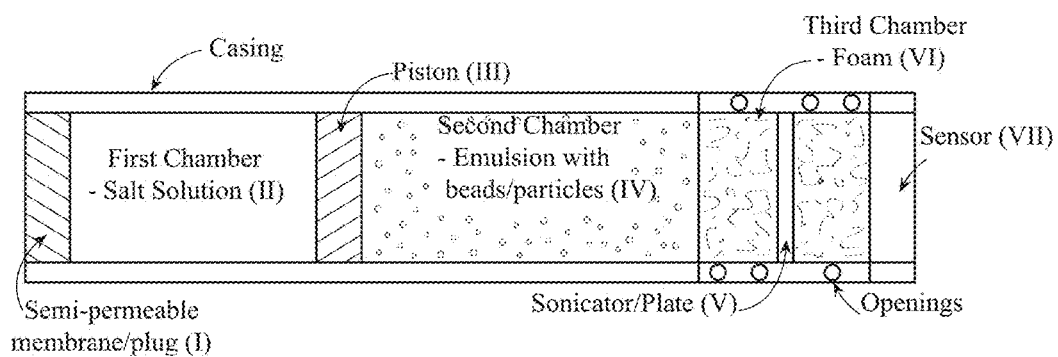
FIG. 1 shows a schematic of an implantable device according to one embodiment disclosed herein.

As used in the specification and claims, the singular forms "a", "an" and "the" include plural references unless the context clearly dictates otherwise. For example, the term "an array" may include a plurality of arrays unless the context clearly dictates otherwise.

Present invention provides a device for controlled delivery of drugs.

"Drug" in context of the present invention may include any therapeutic active agent and/or a biologically active agent (i.e., an active ingredient in a pharmaceutical composition that is biologically active, such as a vaccine), irrespective of the molecular weight of such agents. The terms drug, active, active agent, therapeutic agent are used interchangeably. The term "drug" as used herein refers to a single drug or multiple types of drugs.

In one embodiment, the present invention relates provides a device for controlled delivery of drugs, comprising a micro or nano beads that contains drug, wherein the beads are embedded in a polymer.

"Micro or nano beads" in context of the present invention have an ability to release a drug in a controlled manner. The beads may be spherical or substantially spherical in shape, having its largest transverse dimension is equivalent to the diameter of the bead. Alternatively the bead may be non-spherical, for example, ellipsoidal or tetrahedral in shape having its largest transverse dimension is equivalent to the greatest distance within the bead from one bead surface to another e.g., the major axis length for an ellipsoidal bead or the length of the longest side for a tetrahedral bead.

An embodiment relates to implantable device systems for controlled delivery of drugs, especially for managing therapies for chronic patients. Therapy delivery to treat chronic ailments requires multiple administration of a single or a multiple drug cocktail over a long period of time. Sustained delivery is highly desirable for delivery of bioactive agents particularly biologicals like peptides, antibodies and nucleic acid analogs. This kind of delivery would provide optimum therapeutic efficacy with minimum side effects and thereby improve patient compliance.

More preferably the implantable device therapeutic systems are built from bio-absorbable material. These therapeutic systems deliver the drug to an in vivo patient site and can occupy that site for extended periods of time without being harmful to the host.

In one embodiment, the present invention relates to a device for controlled delivery of drugs, comprising a micro or nano beads that contains drug, wherein the beads are embedded in a flow able mixture such as a liquid, an emulsion or polymer that are approved by the Food and Drug Administration (FDA) for injection into a human body, e.g., a biodegradable sol-gel or biodegradable thermoplastic polymer, including a biodegradable foam that can be squeezed out of the implant.

In one embodiment, the present invention relates to a device for controlled delivery of drugs, comprising a micro or nano beads that contains drug, wherein the device can be implanted into specific organs or underneath the skin for an effective local or systemic delivery of drug.

In one embodiment, the present invention relates to a device for controlled delivery of drugs, comprising a micro or nano beads that contains drug, wherein the device provide sustained drug delivery for a prolonged period of time. Preferably, the time period of ranges from about 1 week to about 5 years. More preferably, the time period of ranges from about 1 month to about 3 years.

The device of the present invention is advantageous over transdermal patches. The transdermal drug delivery system has several limitations since skin forms a very effective barrier and thus the system is suitable for the only medications that have small enough size to penetrate the skin such as molecules having molecular weight less than 500. Further, molecule with sufficient aqueous and lipid solubility, having an octanol/water partition coefficient (log P) between 1 and 3 is required for permeate to transverse subcutaneous and underlying aqueous layers. Patches are known to have side effects like erythema, itching, local edema and allergic reaction can be caused by the drug, the adhesive, or other excipients in the patch formulation. Also dose dumping is one of the serious implications of patch. In one embodiment, the device of the present invention overcomes these limitations of transdermal patch.

In one aspect of this embodiment, the device is pre-loaded in a needle supplied with s disposable applicator.

In one embodiment, the present invention relates to a device for controlled delivery of drugs, comprising a micro or nano beads that contains drug, wherein the device is suitable for delivery of small molecules having molecular weight less than 500 as well as large biologics entities like peptides, antibodies and nucleic acid analogs such as modified RNA, small interfering RNA, anti-sense DNA or fragments thereof.

In one embodiment, the present invention relates to a device for controlled delivery of drugs, comprising a micro or nano beads that contains drug, wherein the device is suitable for delivery of lidocaine, diclofenec, clonidine, estradiol, estradiol/norethindrone acetate, estradiol/levonorgestrel, fentanyl, methylphenidate, nicotine, norelgestromin/ethinyl estradiol, nitroglycerin, oxybutynin, scopolamine, selegiline, testosterone, rivastigmine, rotogotine.

In one embodiment, the present invention relates to a device for controlled delivery of drugs, comprising a micro or nano beads that contains drug, wherein the device is suitable for delivery of long-term sustained release of insulin or analogs thereof, GLP-1 or analogs thereof, alone or in combination of other therapies, to treat diabetes or other metabolic conditions.

In one aspect of this embodiment, the device is suitable for delivery of long-term release of contraceptive hormones, combination of estrogen or progestin or singular delivery of progesterone alone and serves as contraceptive aid for women.

In one aspect of this embodiment, the device is suitable for delivery of long-term therapeutic benefit for ocular diseases, such as age related macular degeneration, dry eye and various others.

In one aspect of this embodiment, the device is suitable for delivery of any small molecule or biologic therapy to treat urinary bladder complications such as incontinence, yeast infections, bladder cancer and various others.

In one aspect of this embodiment, the device is suitable for delivery of therapeutic molecules to the male reproductive organs as a means to treat medical conditions such as erectile dysfunction, premature ejaculation, testicular cancer and various others pertaining to male reproductive system.

In one aspect of this embodiment the device is suitable for delivery of therapeutic molecules to female reproductive organs, uterus and ovaries, to treat medical conditions such as endometriosis, uterine fibroids, ovarian cancer, uterine cancer, poly cystic ovarian syndrome, and various other diseases pertaining to female reproductive system.

In one aspect of this embodiment, the device is suitable for delivery of therapeutic molecules to heart conditions such as heart failure, myocardial ischemia, and various other heart diseases.

In one aspect of this embodiment, the device is suitable for delivery of therapeutic molecules into the adipose tissue to treat conditions such as metabolic syndrome, diabetes, hypercholesterolemia, hypertriglyceridemia and various others.

In another embodiment, the present invention relates to a device for controlled delivery of drugs, comprising a micro or nano beads that contains drug, wherein a top coating can be applied on the beads to delay release of the active agent. In another embodiment, a top coating can be used for the delivery of a second active agent. A layered coating, comprising respective layers of fast- and slow-hydrolyzing polymer, can be used to stage release of the active agent or to control release of different active agents placed in the different layers. Polymer blends may also be used to control the release rate of different active agents or to provide a desirable balance of coating characteristics (e.g., elasticity, toughness) and drug delivery characteristics (e.g., release profile). Polymers with differing solvent solubility can be used to build-up different polymer layers that may be used to deliver different active agents or to control the release profile of active agents.

The amount of an active agent present depends upon the particular the active agent employed and medical condition being treated. In one embodiment, the active agent is present in an effective amount. In another embodiment, the amount of the active agent represents from about 0.01% to about 60% of the coating by weight. In another embodiment, the amount of the active agent represents from about 0.01% to about 40% of the coating by weight. In another embodiment, the amount of the active agent represents from about 0.1% to about 20% of the coating by weight.

Another embodiment relates to a device comprising micro or nano beads having a shell comprising a first material and a second material, wherein the second material comprises a biodegradable material; a core comprising a pharmaceutically effective composition, the core being enclosed by the shell; wherein the first material is distributed in the biodegradable material; wherein the first material is configured to create holes in the shell; wherein the holes allow the pharmaceutically effective composition to be released to the exterior of the shell through the holes. In one embodiment, the shell could be made by polymerizing a silica-functionalized monomer to form a silica-containing biodegradable polymer shell.

Preferably, the first material comprises a metal-containing material that can be heated to form the holes or a biodegradable material that degrades over time. Preferably, the metal-containing material if configured to be heated under radiation, before or after implanting or attaching the device in or on a body of a human or an animal, to form the holes. Preferably, the metal-containing material comprises metallic particles. Preferably, the metallic component comprises an iron-containing material or an iron-containing polymer. Preferably, the metallic particles comprise iron-containing particles or an iron-containing polymer. Preferably, the first material comprises a biodegradable material. Preferably, the first and second materials comprise polymers. Preferably, the first material comprises poly lactid acid (PLA) or an iron-containing polymer and the second biodegradable material comprises poly ε-caprolactone (PCL). Preferably, the core comprises an emulsion or beads of the pharmaceutically effective composition and a polymer.

Preferably, the pharmaceutically effective composition comprises a targeting material or targeting molecule that binds to a certain organ, object or a specific site within a body of a human or an animal.

The implantable device of the embodiments herein can be implanted into specific organs, such as vagina, or underneath the skin for an effective local or systemic delivery of the pharmaceutical agent. In one embodiment, the present invention relates provides device for controlled delivery of drugs, comprising a micro or nano beads that contains drug.

The beads used in the implantable device of the embodiments herein can be made by microfluidics. Microfluidics-based technology enables precise control and manipulation of fluids constrained to micron-sized capillaries. Advantages of microfluidics include reduced sample size and reagent consumption, short processing times, enhanced sensitivity, real-time analysis, and automation. More specifically, drop-based microfluidics allows for the creation of micron-sized emulsions that can hold discrete picoliter volumes, with drop-making frequencies of greater than 2,000 drops per second (2 kHz).

Soft lithography techniques could be employed to fabricate microfluidic devices for bead fabrication. For example, in one embodiment, AutoCAD software was used to generate a UV photomask containing micron-sized capillaries of desired structure and dimension. A silicon wafer was coated with UV photoresist, on which the photomask was placed. After UV exposure, the silicon wafer was developed with propylene glycol monomethyl ether acetate (PGMEA) to generate a positive resist with the desired channels exposed. Polydimethylsiloxane (PDMS) was poured atop the positive resist and incubated at 65° C. overnight. After removing the PDMS (now a negative resist with the desired channels) from the silicon wafer, the inlets were punched and the PDMS was bonded to glass via plasma-activated bonding. The devices were treated with hydrophobic AQUAPEL to prevent the wetting of channels during drop formation. The device for droplet formation is disclosed in U.S. Patent Publication 20120222748, entitled "DROPLET CREATION TECHNIQUES," which is incorporated herein, in relevant parts for the purposes of written description, by reference in its entirety.

Additional U.S. Patents and Publications related to droplet formation and are incorporated herein, in relevant parts for the purposes of written description, by reference in their entirety are:

U.S. Pat. No. 7,776,927 B2—This is a patent broadly describes methods of droplet generation and describes some potential uses in drug delivery.

US20120141589 A1—This patent describes some compounds (such as $CaCO_3$) with which the microfluidic emulsions could be made depending on the drug encapsulated in the emulsion, droplets and beads.

US20130202657—This publication describes a microfoam for drug delivery. Such a microfoam could be incorporated as the foam or mesh in the implantable device of the embodiments herein.

U.S. Pat. No. 6,858,220 B2—This patent discloses an implantable biocompatible microfluidic drug delivery system using only channels, but not microbeads containing a drug.

US20130035574, US20130035660—These publications describe the actual chip/patch rather than the microbeads. However, the publications use microfluidics as well as scaffolding for drug delivery.

U.S. Pat. No. 7,560,036 B2—This patent describes in detail the fabrication of the surface substrate, and uses microneedles for drug delivery.

The drug containing beads could be made from droplets, for example, formed in accordance with the droplet creation techniques disclosed in U.S. Patent Publication US20120222748, for the implantable device of the embodiments by crosslinking biodegradable polymer of the shell of the drug containing beads. The crosslinking density of the biodegradable polymer of the shell could be varied such that even for the same shell thickness, the drug containing beads with low crosslinking density would rupture at earlier time than the drug containing beads with high crosslinking density when the drug containing beads are exposed to blood serum or any other bodily fluid, for example.

The drug containing beads in the embodiments herein can be sustained release particles having an inner core, which could be hollow or solid or porous, containing an active pharmaceutical ingredient, an optional intermediate coating substantially surrounding the inner core, and an outer coating substantially surrounding the optional intermediate coating comprising a pH independent polymer such as that disclosed in U.S. Patent Publication 20080187579, entitled "Extended-release dosage form," which is incorporated herein, in relevant parts for the purposes of written description, in its entirety. The implantable device of the embodiments herein could have two or more bead populations wherein each of the bead populations has a different drug release profile. The method of preparing an extended release dosage composition comprising one or more bead populations could be that disclosed in U.S. Patent Publication 20080187579, with an additional requirement that the beads are made of biodegradable material such as a biodegradable polymer.

In one embodiment, the present invention relates to a device for controlled delivery of drugs, comprising a micro or nano beads that contains drug, wherein the beads comprise a biocompatible, cross-linked, biodegradable material, collagen, fibronectin, elastin, hyaluronic acid or a mixture thereof.

In one embodiment the biodegradable polymer material for the bead and foam and/or any other material of the device may include polyglycolic acid ("PGA"), polylactic acid ("PLA"), polycaprolactic acid ("PCL"), poly-p-dioxanone ("PDO"), PGA/PLA copolymers, PGA/PCL copolymers, PGA/PDO copolymers, PLA/PCL copolymers, PLA/PDO copolymers, PCL/PDO copolymers or combinations therof.

In another embodiment, the biodegradable polymer material may include polycarbonate polyurethanes, polycarbonate urea-urethanes, polyether polyurethanes, poly(carbonate-co-ether) urea-urethanes, polysiloxanes and the like.

The implantable device could include a device such as a monitor/transmitter with ability to detect blood glucose levels, sense hormonal levels, and/or detect body temperature. The implantable device could include a device such as a monitor/transmitter an ability to communicate to the sensors/detectors in smartphone, an ability to transmit data to iCloud, and/or an ability to sense appetite sensing hormones.

Implant Device

FIG. 1 is a schematic diagram showing the implantable device based on an osmotic pump delivery system, with several features explained below. An osmotic pump delivery is disclosed in some of the following US patents and applications of Intarcia Therapeutics, Inc., which are incorporated herein, in relevant parts for the purposes of written description, by reference in their entirety:

| Title | Application | Publication | Patent |
|---|---|---|---|
| DEVICES, FORMULATIONS, AND METHODS FOR DELIVERY OF MULTIPLE BENEFICIAL AGENTS | 12378341 Feb. 12, 2009 | 20090202608 Aug. 13, 2009 | 8343140 Jan. 1, 2013 |
| TWO-PIECE, INTERNAL-CHANNEL OSMOTIC DELIVERY SYSTEM FLOW MODULATOR | 13601939 Aug. 31, 2012 | 20120330282 Dec. 27, 2012 | 8367095 Feb. 5, 2013 |
| SUSTAINED DELIVERY OF AN ACTIVE AGENT USING AN IMPLANTABLE SYSTEM | 13645124 Oct. 4, 2012 | 20130035669 Feb. 7, 2013 | 8535701 Sep. 17, 2013 |
| RAPID ESTABLISHMENT AND/OR TERMINATION OF SUBSTANTIAL STEADY-STATE DRUG DELIVERY | 13645422 Oct. 4, 2012 | 20130030417 Jan. 31, 2013 | |
| OSMOTIC DELIVERY SYSTEMS AND PISTON ASSEMBLIES FOR USE THEREIN | 12930950 Jan. 19, 2011 | 20110166554 Jul. 7, 2011 | 8801700 Aug. 12, 2014 |
| SELF ADJUSTABLE EXIT PORT | 09045944 Mar. 23, 1998 | | 5997527 Dec. 7, 1999 |
| OSMOTIC DELIVERY SYSTEM AND METHOD FOR ENHANCING START-UP & PERFORMANCE OF OSMOTIC DELIVERY SYSTEMS | 08970530 Nov 14, 1997 | | 6132420 Oct. 17, 2000 |
| IMPLANTER DEVICE FOR SUBCUTANEOUS IMPLANTS | 09217824 Dec. 22, 1998 | | 6190350 Feb. 20, 2001 |
| OSMOTIC DELIVERY SYSTEM | 09121878 Jul. 24, 1998 | | 6287295 Sep. 11, 2001 |
| SEMIPERMEABLE BODY ASSEMBLY | | | |
| RATE CONTROLLING MEMBRANES FOR CONTROLLED IMPLANTS | 09213213 Dec. 17, 1998 | | 6375978 Apr. 23, 2002 |
| VALVE FOR OSMOTIC DEVICES | 09748099 Dec. 21, 2000 | | 6508808 Jan. 21, 2003 |
| OSMOTIC DELIVERY SYSTEM FLOW MODULATOR APPARATUS AND METHOD | 09122073 Jul. 24, 1998 | | 6524305 Feb. 25, 2003 |
| OSMOTIC DELIVERY SYSTEM HAVING SPACE EFFICIENT PISTON | 09472600 Dec. 27, 1999 | | 6544252 Apr. 8, 2003 |
| OSMOTIC DELIVERY SYSTEM HAVING SPACE EFFICIENT PISTON | 10354142 Jan. 30, 2003 | 20030139732 Jul. 24, 2003 | 6872201 Mar. 29, 2005 |
| MINIMALLY COMPLIANT, VOLUME-EFFICIENT PISTON FOR OSMOTIC DRUG DELIVERY SYSTEMS | 10606407 Jun 25, 2003 | 20040019345 Jan. 29, 2004 | 6939556 Sep. 6, 2005 |
| OSMOTIC DELIVERY DEVICE HAVING A TWO-WAY VALVE AND A DYNAMICALLY SELF-ADJUSTING FLOW CHANNEL | 10302104 Nov. 21, 2002 | 20040102762 May 27, 2004 | 7014636 Mar. 21, 2006 |
| SUSTAINED DELIVERY OF AN ACTIVE AGENT USING AN IMPLANTABLE SYSTEM | 10645293 Aug. 20, 2003 | 20040039376 Feb. 26, 2004 | 7655257 Feb. 2, 2010 |
| OSMOTIC DELIVERY SYSTEMS AND PISTON ASSEMBLIES FOR USE THEREIN | 12658570 Feb. 9, 2010 | 20100185184 Jul. 22, 2010 | 7879028 Feb. 1, 2011 |

"Intarcia's platform technology is known as the DUROS® subcutaneous delivery system. The DUROS system is comprised of a small, matchstick-sized osmotic pump that is inserted subcutaneously (just beneath the skin) to deliver a slow and consistent flow of medication. Each device contains an appropriate volume of drug product to treat a patient for a predetermined extended duration of time. The DUROS device is activated when subcutaneous tissue fluid passes through the device inlet, expanding the osmotic engine. The osmotic engine drives the piston at a constant rate, delivering consistent drug levels through the device outlet. The device can be inserted in a subcutaneous space in various locations on the arms and abdomen during a reimbursable in-office procedure, in as little as five minutes by a physician or physician's assistant, and ensures 100 percent patient adherence to therapy. Delivering drugs via the DUROS technology avoids unwanted peak drug levels often associated with toxicities and sub-therapeutic troughs often associated with suboptimal therapeutic effects. Another key aspect of the DUROS technology is the unique formulations that maintain stability of proteins and peptides at human body temperature for extended periods of time. This advance in formulations allows continuous delivery of effective therapy with less frequent administration thereby ensuring compliance and improving patient convenience. The DUROS device was first used as a drug delivery technology for the FDA-approved product Viadur® in the delivery of leuprolide acetate." Source: http://www.diabetesincontrol.com/wp-content/uploads/2011/09/www.diabetesincontrol.com_images_issues_2011_09_ntarcia_platform_technology.pdf. "Intarcia's clinical stage type 2 diabetes candidate, ITCA 650 involves the delivery of exenatide, an approved incretin mimetic using the DUROS delivery system. The DUROS delivery system is a matchstick-sized device consisting of a cylindrical titanium alloy reservoir. Once inserted under the skin, water from the extracellular fluid enters the device at one end, by diffusing through a semipermeable membrane directly into a salt osmotic engine that expands to drive a piston at a controlled rate of travel. This forces the drug formulation to be released in a slow and consistent fashion through the exit port, or diffusion moderator at the other end of the device." Id.

Figure 2:
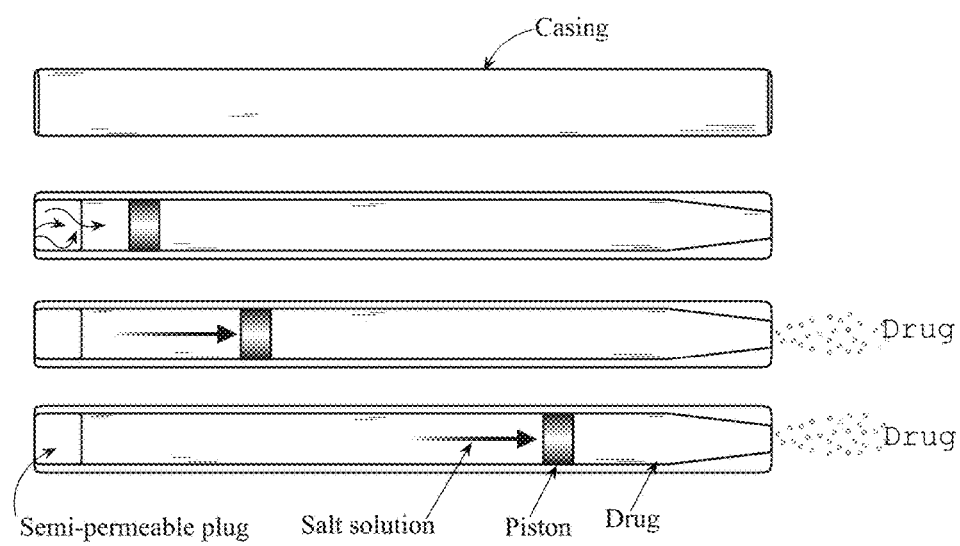
FIG. 2 (prior art) is a diagram showing how DUROS' implantable device works.

A diagram showing how DUROS' implantable device works is shown in FIG. 2 (prior art).

In the implantable device shown in FIG. 1, here are three specific chambers and therefore four barriers separating these chambers from one another. Let us start by describing the device from the left side, and work our way to the right. On the left end of the device there is a semi-permeable plug, or more specifically, an osmotic membrane (I). This membrane would allow for fluid from the body to flow into the device. The diffusion mechanism is osmosis because in the first chamber (II), there is a highly concentrated salt solution (>1000 nM as the physiological ionic concentration in the human body is about 150 nM) that will result in liquid being drawn into the implant. As liquid is drawn into the chamber, its volume increases, and this pressure pushes the piston (III), which could made of a magnetic material, between the first and second chambers to the right. The cylinder surrounding the piston III is preferably made of a non-magnetic material, such as a non-magnetic metal or a non-magnetic ceramic material. The non-magnetic metal could be titanium and stainless steel to cobalt-chromium, tungsten, and tantalum, or a host of metals that are used in cardiovascular, orthopedic, and many other medical device fields, so long these metals are non-magnetic.

As the piston is pushed to the right by osmotic pressure, it decreases the volume of the middle chamber (IV). This chamber contains the drug in beads in a flow able mixture, which could be an emulsion, and is interchangeably referred to as "emulsions." The beads could be 10-100 µm in diameter, and have shell made of a material is stimuli-responsive polymer, preferably a stimuli-responsive biodegradable polymer, such as those disclosed in U.S. Patent Publication 20060127925, entitled "Stimuli-responsive polymer conjugates and related methods," U.S. Patent Publication 20160263221, entitled "MULTI-RESPONSIVE TARGETING DRUG DELIVERY SYSTEMS FOR CONTROLLED-RELEASE PHARMACEUTICAL FORMULATION," U.S. Patent Publication 20170119785, entitled "SOL-GEL POLYMER COMPOSITES AND USES THEREOF," U.S. Patent Publication 20170165201, entitled "PH-RESPONSIVE MUCOADHESIVE POLYMERIC ENCAPSULATED MICROORGANISMS," U.S. Patent Publication 20170135953, entitled "METHODS FOR LOCALIZED DRUG DELIVERY," U.S. Patent Publication 20170073311, entitled "SUPRAMETALLOGELS AND USES THEREOF," and U.S. Patent Publication 20170065721, entitled "SYNTHESIS AND USE OF THERAPEUTIC METAL ION CONTAINING POLYMERIC PARTICLES" which are incorporated, in relevant parts for the purposes of written description, herein by reference in its entirety. The stimuli-responsive polymer could be a temperature-sensitive polymer, a pH-sensitive polymer, an electrical or magnetic field-sensitive polymer, or a light-sensitive polymer. An example of a stimuli-responsive polymer is poly(N-isopropylacrylamide). A pH-sensitive polymer could dissociate or dissolve at the blood pH of between 7.35 and 7.45. For example, the shell could be made of a polymer held together by a polymer cross linker. The polymer could be a pH-sensitive or a temperature-sensitive polymer that dissociates or dissolves at the blood pH of about 7.4 or the normal human body temperature of 36.5-37.5° C. (97.7-99.5° F.). Thus, the pH of this chamber within the implantable device would be lower than that of blood (below, 6.5, preferably below 5, e.g., between 1-3) or higher than that of blood (above 8, preferably above 10, e.g., between 11-14), preventing any of the drug molecules from exiting through the beads in the acidic or basic flowable mixture (e.g., emulsion) within the implant. Once the beads reach the blood stream, however, the drug would begin coming out of the beads as the beads dissociate or dissolve in blood. The shell of the bead could also contain an antibody for tumor targeting in the case of cancer as well as gold particles to enhance radiation therapy. These are discussed in more detail in a later section.

As the piston gets pushed to the right, some of the bead-containing emulsion in the second middle chamber flows to the final chamber (VI). This third chamber would contain a foam, e.g., a biodegradable foam, that works as the flow control mechanism. The emulsions would pass through the porous foam before reaching the 100-500 µm openings bordering the circumference of chamber VI. These openings release the bead-containing emulsion from the implantable device to the blood stream. The foam would act to prevent blood from entering the device and back-filling it. In addition to just acting as an obstruction between the device and the blood, the foam can act to control the flow rate of the emulsions from the device to the body. More specifically, the foam will have the property that it can be made more porous when sonicated. Thus, when the flow rate of the drug into the blood stream is smaller than desired, sonication can be used to create more porosity in the foam. Another way of creating greater porosity through the foam would be through a controlled explosion within the foam. Thereby, as the foam disintegrates, it is easier for the emulsions to traverse from the middle chamber out into the body.

The open cell biodegradable foam could be reticulated foam formed after thermal reticulation such those disclosed in U.S. Pat. No. 8,801,801, entitled "AT LEAST PARTIALLY RESORBABLE RETICULATED ELASTOMERIC MATRIX ELEMENTS AND METHODS OF MAKING SAME," which is incorporated herein, in relevant parts for the purposes of written description, in its entirety. In the biodegradable reticulated foam, the boundary skin layer formed during the foaming process was trimmed and removed prior to subjecting the as-made foam to thermal reticulation. The open cell biodegradable foam in the embodiments herein is generally resilient to crushing when implanted within the body of a human or animal; thereby the open cell biodegradable foam substantially maintains its original shape before implantation even after implantation within the body of the human or animal.

Figure 3:
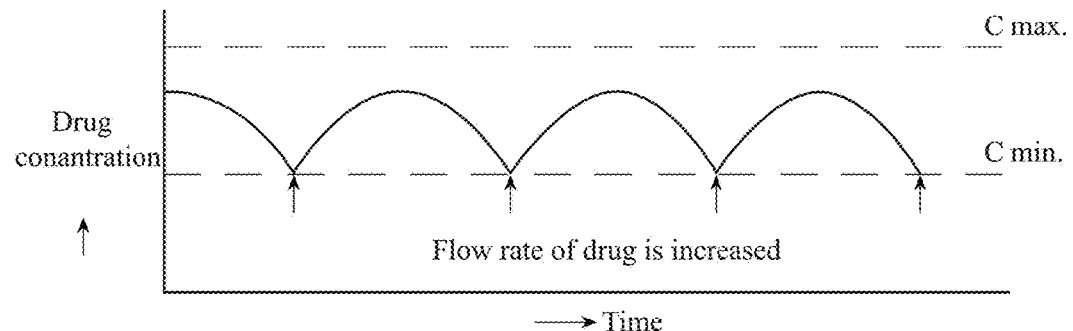
FIG. 3 shows a schematic of a substantially constant drug concentration profile with time according to one embodiment disclosed herein.

It is preferable to be able to control the flow rate of drug release to have a multifunctional implant. More specifically—assuming that we want a constant output of the pharmaceutical product—as liquids from the body enter the first chamber on the left due to osmosis, the pressure on the piston will diminish over time. Thus, the rate at which drug exits the implantable device will also decrease over time. To solve this problem, the implantable device will have a sensor on or in the rightmost side wall (VII), e.g., an impermeable plug, and the sensor will measure the concentration of drug in the blood at that spot. When the concentration is below the desired threshold, the sensor will indicate to the on-implant sonicator (V) to turn on for a set number of seconds. This sonicator is the barrier between the second and third chambers or within the third chamber as shown in FIG. 1, and as it sonicates, the foam will degrade, making easier access for the drug-containing emulsions to reach the openings bordering the blood stream. In this manner, the drug is released with a substantially constant concentration if the concentration of the drug is within limits of Cmax and Cmin as shown in FIG. 3.

The limits of Cmin and Cmax are 80% to 125% of a desired concentration (which would be between the limits of Cmin and Cmax in FIG. 3) of the drug in the body of the human or animal. These limits of Cmin and Cmax are selected in the context of this invention because the United States FDA considers two products bioequivalent if the 90% confidence interval of the peak concentration of a drug in the blood serum of a test sample (e.g. generic formulation) to reference (e.g. innovator brand formulation) is within 80% to 125% of a desired concentration of a drug in the blood serum.

The desired concentration could be substantially constant with time. The desired concentration could be substantially constant for a first period of time and substantially zero for a second period of time, or vice-versa, or any combinations thereof. The desired concentration could be increasing or decreasing with time, or any combinations thereof.

In addition to dissolving or degrading the foam to increase the porosity of the foam and thereby increase the flow rate of the device, it may be necessary to lessen or even completely stop the drug release in certain circumstances. This can be done by applying an external magnet, such as an electromagnet, atop the implantable device to prevent the piston, which could be made of magnetic material, from moving despite osmotic pressure. The strength of the magnetic force would be greater than that of the fluid pressure, thereby stalling the piston. Since the implantable device will be inserted either in the arm or near the stomach, such a magnet could be applied on an armband or belt surrounding the device. Such a capability would allow a patient to temporarily stop drug release completely. Also, in case it is difficult to sonicate the biodegradable foam internally, a sonicator can be applied externally on such an armband or belt. In this case, the biosensor for drug concentration could send a signal to the patient (perhaps a text message to a phone or an email to a computer) indicating that the patient must apply the sonicator.

Figure 4:
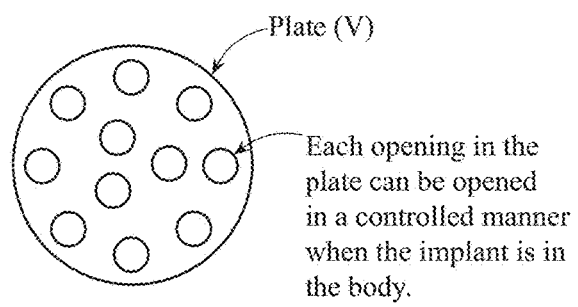
FIG. 4 shows a schematic of a plate containing holes, some or all of which that are filled with phase-change material (PCM).

Further, instead of or in addition to having a foam for controlled release of the emulsions, the implantable device could encompass a plate in lieu of or in addition to the sonicator (both are shown with numeral V in FIG. 1), as shown in FIG. 4, containing holes, some or all of which that are filled with phase-change material (PCM) Similar to the physical (sonification) dependence of the state of the foam and the chemical (pH) dependence of the state of the emulsions, the PCM is temperature-dependent. Thus, when the sensor indicates that there is not enough drug in the blood stream, the patient could add heat to the implantable device via the external belt or armband in order to melt the PCM and unclog the holes. As these holes are opened up, the bead-containing emulsion from the middle chamber will be flow more easily into the third chamber and eventually leave the device. Hence, this would be an alternative rate control mechanism.

In another embodiment, the first chamber containing the salt solution and the second chamber containing the bead-containing emulsion can be recharged, for example, using a syringe containing the salt solution or the bead-containing emulsion, even when the implantable device is implanted in the body of the human or animal without removing the implantable device from the body. This could be done through one or more hermetically-sealed valves in the casing, with the valves located in positions above the first and second chambers. The hermetically-sealed valve could be a pneumatically sealed valve or a slit valve such as those disclosed U. S. Patent Publication 20140142556, entitled "IMPLANTABLE DRUG DELIVERY DEVICES" which is incorporated, in relevant parts for the purposes of written description, herein by reference in its entirety.

One way to refresh and/or increase the osmotic pressure of the salt solution in the first chamber after implantation of the implantable device in the body would be to extract the used salt solution from the first chamber and replace it with a fresh salt solution. Similarly, one way to refresh and/or increase the concentration of the drug in the second chamber after implantation of the implantable device in the body would be to extract the used emulsion containing the drug-containing beads from the second chamber and replace it with a fresh emulsion containing the drug-containing beads or add a fresh emulsion containing the drug-containing beads without removing the existing emulsion from the second chamber.

In another embodiment, the emulsion containing the drug-containing beads could contain multiple drugs (a cocktail of drugs). In this case, different drugs could be encapsulated in different types of beads, with the different types of beads having certain affinity for binding to different organs or tissues of the body, such as though different functional groups attached to the different types of beads.

Figure 5:
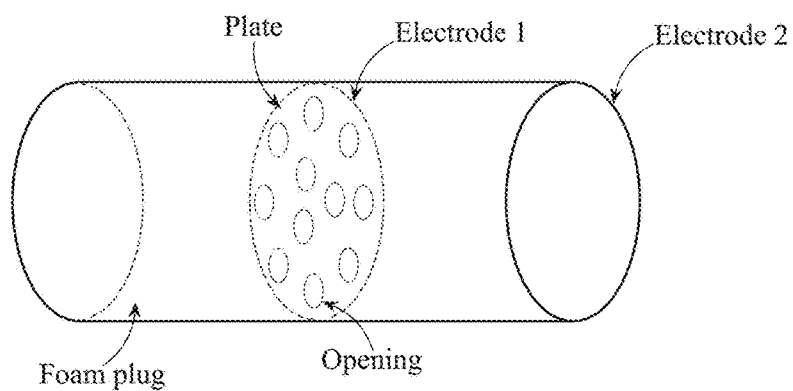
FIG. 5 shows a schematic of a foam plug containing the plate of FIG. 4, further showing electrodes 1 and 2 across the foam plug.

FIG. 5 shows a foam plug with a plate of FIG. 4 located within the plug. The plate could also function as an electrode (electrode 1) with a counter electrode (electrode 2) located at around one end of the foam plug. The combination of electrodes 1 and 2 could be used for creating holes in the plate of FIG. 4 or to enhance or slow down the flow rate by electrophoresis, which causes the motion of dispersed particles relative to a fluid under the influence of a spatially uniform electric field.

Figure 6:
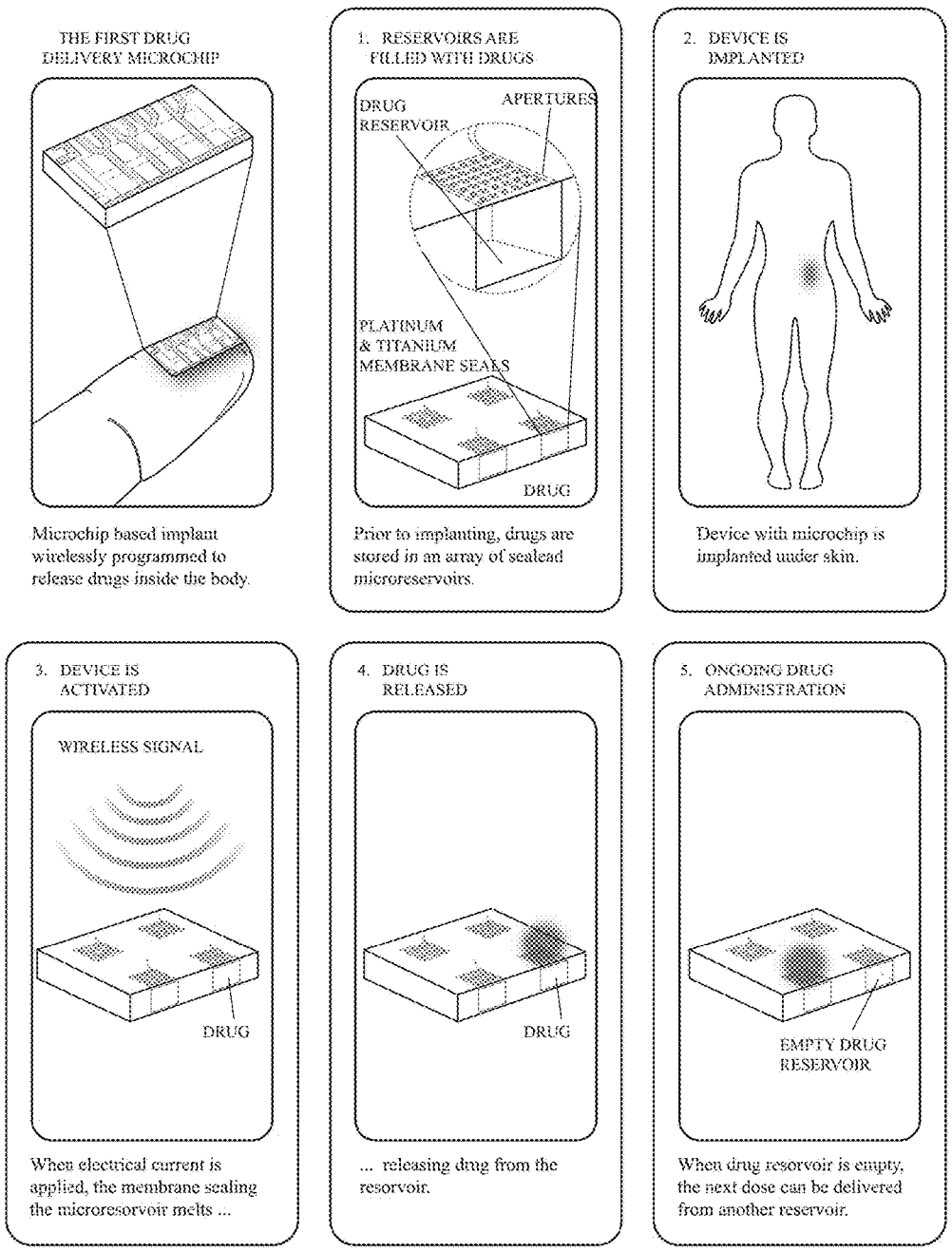
FIG. 6 (prior art) is a schematic showing how 'MICRO-CHIPS' wireless implantable device works.

Also, instead of applying external heat, the implantable device could internally contain electrodes that heat the PCM plate and dissolve some of the clogged holes. Different-sized holes could be plugged with PCMs of different melting points to ensure greater flexibility in controlling flow rate. MICROCHIPS technology, which was originally created in the 1990s by MIT researchers Robert Langer and Michael Cima and PhD student John Santini, and later licensed it out to MICROCHIPS. A diagram showing how MICROCHIPS' wireless implantable device works is shown in FIG. 6 (prior art). The following are the US patents of Langer and Cima, and these US patents are incorporated herein, in relevant parts for the purposes of written description, in their entirety by reference.

U.S. Pat. No. 8,403,907 Full-Text Method for wirelessly monitoring implanted medical device U.S. Pat. No. 8,308,707 Full-Text Method and system for drug delivery to the eye U.S. Pat. No. 7,918,842 Full-Text Medical device with controlled reservoir opening U.S. Pat. No. 7,901,397 Full-Text Method for operating microchip reservoir device U.S. Pat. No. 7,892,221 Full-Text Method of controlled drug delivery from implantable device U.S. Pat. No. 7,879,019 Full-Text Method of opening reservoir of containment device U.S. Pat. No. 7,776,024 Full-Text Method of actuating implanted medical device U.S. Pat. No. 7,354,597 Full-Text Microscale lyophilization and drying methods for the stabilization of molecules U.S. Pat. No. 7,226,442 Full-Text Microchip reservoir devices using wireless transmission of power and data U.S. Pat. No. 7,070,592 Full-Text Medical device with array of electrode-containing reservoirs U.S. Pat. No. 7,070,590 Full-Text Microchip implants U.S. Pat. No. 6,976,982 Full-Text Flexible microchip devices for ophthalmic and other applications U.S. Pat. No. 6,808,522 Full-Text Microchip devices for delivery of molecules and methods of fabrication thereof U.S. Pat. No. 6,537,256 Full-Text Microfabricated devices for the delivery of molecules into a carrier fluid U.S. Pat. No. 6,491,666 Full-Text Microfabricated devices for the delivery of molecules into a carrier fluid U.S. Pat. No. 6,123,861 Full-Text Fabrication of microchip implants U.S. Pat. No. 5,797,898 Full-Text Microchip implants U.S. Pat. No. 5,514,378 Full-Text Biocompatible polymer membranes and methods of preparation of three dimensional membrane structures Similar technology as that disclosed in the patents of Langer and Cima can also be employed to generate controlled explosions of PCMs by generating electrical current and burning or melting the PCM membrane sealing the holes, thereby unplugging the holes. The explosions in the plate with PCM in holes can be done similar to that in the MicroCHIPS implant, for example, as and when required using a controller appropriately spaced apart electrodes, either directly and automatically based on feedback from the sensor or externally by a person using a remote control device. Also, the explosions can be programmed ahead of time into the implantable device when there is a reliably tested dosage cycle and the patient does not want make adjustments real-time.

Furthermore, some of the openings bordering the circumference of chamber VI can also be filled with phase-change material (PCM). These openings could be explosively opened as explained above in the context of opening the holes in the plate V of FIG. 4 wherein the holes that are filled with phase-change material (PCM).

Besides the sensor being attached to the implant, there could be a secondary sensor inserted elsewhere in the body, preferably near a target site. The secondary sensor could be a biodegradable sensor, for example, such as that developed by a team from University of Illinois in Urbana and Washington University in St. Louis and published in the Jan. 18, 2016, issue in the journal Nature, and subsequently disclosed on Jan. 26, 2017, in U.S. Patent Publication 20170020402, entitled "IMPLANTABLE AND BIORESORBABLE SENSORS," which is incorporated herein, in relevant parts for the purposes of written description, in its entirety by reference.

Furthermore, the micro or nano beads could be of two or more types—those that rapidly break-up as soon as they leave the implantable device and those that break-up after a longer period (several days) after exiting the implantable device and travelling to the target site. The shell of the rapidly disintegrating beads could contain starch or cellulose.

In one embodiment, it is not necessary to include the first chamber and have an osmosis-driven piston. Instead, the piston could be driven by electro-magnetically using electromagnets in a device external to the body in which the implantable device is implanted. In this case, the external device could be manufactured with circuitry that controls the movement of the piston. This system would allow extremely precise flow rates for the emulsions based on feedback from the sensor attached to the implantable device or the secondary sensor inserted elsewhere in the body, preferably near a target site. The sensors could send signals indicating when to push, pull, or stop the piston entirely to allow for pre-programmed drug release for the patient.

The implantable device of the embodiments herein may require an energy source that is biocompatible and produces electricity. The energy source could be as a battery, photo-energy source, or a galvanic cell. The batteries in the implantable device of the embodiments could be charged externally by radio-frequency (RF) charging.

In terms of target specificity for the beads, especially in the case of cancer, it is important to lead the drug-encapsulated beads to the tumor site. Thus, each bead will contain an antibody, corresponding to antigens on the site of the tumor, on its surface. The antibody would be joined by a linker to the shell of the bead, and ensure that the drug is attracted toward the tumor as opposed to just free-floating in the blood. If the site of the tumor is known in advance, an additional sensor could also be placed there to measure drug concentration. This sensor can communicate with the sensor on the implantable device and thereby request for greater drug release in case the tumor is not being properly attacked. This interplay between sensors would greatly define the conditions for controlled drug release. In addition, these beads could have gold or platinum (or any other inert metal) attached to the surface of the beads, e.g., composite inorganic organic nanoclusters (COINs), to tremendously help patients undergoing radiotherapy. For example, U.S. Patent Publication 20160129111, entitled "METHODS FOR DELIVERING AN ANTI-CANCER AGENT TO A TUMOR," which is incorporated herein, in relevant parts for the purposes of written description, herein by reference in its entirety, discloses methods for delivering an anti-cancer agent to a tumor in a subject. The method involves administering to the subject (i) gold particles and (ii) at least one-anti-cancer agent directly or indirectly bonded to the macromolecule and/or unbound to the macromolecule; and exposing the tumor to light for a sufficient time and wavelength in order for the gold particles to achieve surface plasmon resonance and heating the tumor.

COINs are composed of a metal, preferably an inert metal such as gold or platinum, and at least one organic radiation-active compound. For example, Raman-active COINs are disclosed in U.S. Pat. No. 7,790,286, which is incorporated herein, in relevant parts for the purposes of written description, in its entirety by reference. Interactions between the metal of the clusters and the radiation-active compound(s) enhance the radiation signal obtained from a radiation-active compound when the nanoparticle is excited. Since a large variety of organic radiation-active compounds can be incorporated into the nanoclusters, a set of COINs can be created in which each member of the set has a radiation enhancement unique to the set. Also, COINs can also function as sensitive reporters for highly parallel detection of the beads. Furthermore, treatment specificity can be enhanced by incorporating thousands of gold or platinum particles into a single nanocluster and/or attaching multiple nanoclusters to a single bead.

More specifically, once the beads are attached to the tumor site, the gold or platinum particles amplify the radiation that is presented at the tumor site, preventing the need for exorbitantly high levels of radiation that can oftentimes be dangerous to the individual. Thus, through the combination of a target antibody, a sensor at the tumor site, and gold/platinum particle technology, the implantable device would address the issue of treatment specificity, which is incredibly problematic in oncology care.

In one embodiment, the nano or micro beads could comprise a shell comprising a first material and a second material, wherein the second material comprises a biodegradable material; a core comprising a pharmaceutically effective composition, the core being enclosed by the shell; wherein the first material is distributed in the biodegradable material; wherein the first material is configured to create holes in the shell; wherein the holes allow the pharmaceutically effective composition to be released to the exterior of the shell through the holes. In one embodiment, the shell could be made by polymerizing a silica-functionalized monomer to form a silica-containing biodegradable polymer shell.

In the implant, the pharmaceutically effective composition could comprise a targeting material or molecule that binds to a certain organ, object or a specific site within a body of a human or an animal. Thus, for example, even if the drug is the same but used for different cancers, then using a targeting molecule for a particular type of cancer, e.g., breast cancer, then the drug would bind to the cells of that particular type of cancer. On the other hand, if the drug is intended for ovarian cancer, then the target molecule could be specifically one that binds to the cells of ovarian cancer. The targeting material or molecule could be a biomarker.

An ingredient of the pharmaceutically effective composition could be a material that prevents the pharmaceutically effective composition from being taken up by the host defense as white blood and macrophages in the human or animal body. Such an ingredient remains in the blood but the body organs cannot take it up. An example of such an ingredient is polyethylene glycol (PEG), e.g., having 200 Dalton molecular weight.

In another embodiment, the biodegradable shell of the nano or micro beads could contain a controlled release ingredient that functions as a control release sensor to control the release of the drug. For example, one would want a particular concentration of the drug at a given site over a given extended period of time. The control release ingredient could be a material that degrades faster than the remaining material of the biodegradable shell of the nano or micro beads or punches holes (pores) in biodegradable shell of the nano or micro beads.

The holes in the biodegradable shell of the nano or micro beads could be punched by giving external stimuli such as sound, such as ultrasonic sound, radio frequency heating, radiation or microwave to the drug containing beads. The external stimulus heats up the controlled release ingredient, thereby punching one or more holes in the shell surrounding the controlled release ingredient, which could be a metal-containing material is configured to form holes in the shell, before or after implanting or attaching the device in or on a body of a human or an animal, when the shell is exposed to an external stimulus. For example, the controlled release ingredient that can be used for punching holes in the shell could be molecular iron such a magnetic resonance imaging (MRI) contrast agent. Depending on the concentration of the controlled release ingredient, one can control the number of holes punched in the shell, which in turn controls the amount of drug released from the core to the outside of the shell.

Two types of iron oxide MRI contrast agents exist: superparamagnetic iron oxide (SPIO) and ultra small superparamagnetic iron oxide (USPIO). These contrast agents consist of suspended colloids of iron oxide nanoparticles. A FDA approved iron oxide MRI contrast is LUMIREM (also known as GASTROMARK).

Other controlled release ingredients for punching holes in the shell could be superparamagnetic iron platinum particles (SIPPs). SIPPs could also encapsulated with phospholipids to create multifunctional SIPP stealth immunomicelles that specifically targeted human prostate cancer cells.

Yet, other controlled release ingredients for punching holes in the shell are Mn-based nanoparticles. Manganese ions (Mn2+) are often used as a contrast agent in animal studies, usually referred to as MEMRI (Manganese Enhanced MRI). For example, Mn2+ carbon nanostructure complexes of graphene oxide nanoplatelets and graphene oxide nanoribbons could also be used as controlled release ingredients.

In addition to or in lieu of the osmotic pump option of pumping the emulsion from the pump chamber containing the emulsion could be by using shape memory alloy (e.g., nitinol) spring that is connected to the piston and attached to a hook inside the implantable device opposite the piston. For example, the hook could be attached to the plate V shown in FIG. 4 and discussed above, or the front end of the implantable device attached to the wall on the right side of the third chamber (IV) in FIG. 1. The shape memory alloy spring could be heated using external heating, e.g., radio frequency heating.

The advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

Uses Thereof:

Use of such device for systemic delivery any active pharmaceutical ingredient in humans or animals, as a patient convenience to avoid daily, weekly or monthly oral, subcutaneous or intravenous administration.

Use of such device for systemic delivery any biologic therapy in humans or animals as a means of patient convenience to overcome daily, weekly or monthly oral, subcutaneous or monthly administration. Biologic molecules can be peptides, antibodies or fragments thereof, nucleic acid molecules such as modified RNA, small interfering RNA, anti-sense DNA molecules or fragments thereof.

Use of such device to deliver antigens to elicit vaccine responses in humans or animals.

Use of such device to provide local tissue delivery of any therapeutic molecule, be it small molecule or biologic.

Use of such device to provide long-term sustained release of insulin or analogs thereof, alone or in combination of other therapies, to treat diabetes or other metabolic conditions.

Use of such device to provide long-term sustained release of GLP-1 or analogs thereof, alone or in combination of other therapies, to treat diabetes or other metabolic conditions.

Deposition of such device underneath the skin, or in fat tissue or in any specific organ for the purpose of long-term release of any therapeutic molecule, be it either a small molecule or biologic.

Specific use of such device to provide sustained long-term release of contraceptive hormones, combination of estrogen or progestin or singular delivery of progesterone alone and serve as contraceptive aid for women.

Specific use of such device for the intraocular delivery of any small molecule or biologic therapy as a means to provide the long-term therapeutic benefit for ocular diseases, such as age related macular degeneration, dry eye and various others. Deposition of such device and use to directly into bladder for long-term delivery of any small molecule or biologic therapy to treat urinary bladder complications such as incontinence, yeast infections, bladder cancer and various others.

Deposition of such device and use to locally deliver therapeutic molecules to the male reproductive organs as a means to treat medical conditions such as erectile dysfunction, premature ejaculation, testicular cancer and various others pertaining to male reproductive system.

Deposition of such device and use to locally deliver therapeutic molecules to female reproductive organs, uterus and ovaries, to treat medical conditions such as endometriosis, uterine fibroids, ovarian cancer, uterine cancer, poly cystic ovarian syndrome, and various other disease pertaining to female reproductive system.

Deposition of such device and use to locally deliver therapeutic molecules to heart conditions such as heart failure, myocardial ischemia, and various other heart diseases.

Deposition of such device and use to locally deliver therapeutic molecules into the adipose tissue to treat conditions such as metabolic syndrome, diabetes, hypercholesterolemia, hypertriglyceridemia and various others.

In embodiments herein, depending on the dosing requirements of a particular drug, the device can provide a constant drug concentration or even an increasing drug concentration or a decreasing drug concentration over time. The device can also provide a constant concentration for a certain amount of time, followed by no drug release for some time, and subsequently followed by the same concentration from the beginning. This would be especially useful in the case of birth control medication; for a short period of time when a woman wants to get pregnant, the implantable device can stop the release of the drug, and then continue it again afterwards. Thus, embodiments herein relate to a highly controlled delivery system by which any permutation of drug release profiles could be either programmed ahead of time or even implemented in real-time.

INCORPORATION BY REFERENCE

All patents, application and publications referred to in this application are incorporated herein, in relevant parts for the purposes of written description, by reference in their entirety.

The invention claimed is:

1. An implantable device comprising:
a casing, a semi-permeable membrane plug at or near a first end of the casing, a piston, beads, and an opening for release of the beads from the implantable device within a body of a human or an animal;
a sensor configured to monitor a concentration of a drug in the body of the human or the animal;
a side wall at or near a second end of the casing, wherein the casing is substantially tubular having at least the first end of the casing and the second end of the casing, and the second end of the casing is opposite the first end of the casing;
a sonicator, wherein the sonicator is located between the piston and the side wall;
a first chamber between the semi-permeable membrane plug and the piston, a second chamber between the piston and the sonicator, and a third chamber between the second chamber and the side wall, wherein the first chamber comprises a salt solution, the second chamber comprises the beads, and the third chamber comprises a foam;
wherein the implantable device is configured to be implanted within the body of the human or the animal during delivery of the beads into the body of the human or the animal;
wherein the beads comprise a core and a shell with the core being enclosed by the shell and the beads contain the drug; and
wherein the implantable device is configured to produce a desired flow rate of elution of the drug from the implantable device when the implantable device is implanted within the body of the human or the animal, wherein the sonicator is configured to sonicate and increase porosity of the foam.

2. The implantable device of claim 1, wherein the drug and/or the beads comprise a targeting material or a targeting molecule that binds to a certain organ, tissue, object or a specific site within the body of the human or the animal.

3. The implantable device of claim 1, wherein the shell comprises a stimuli-responsive polymer configured to break the shell, before or after implanting or attaching the implantable device in or on a body of a human or an animal, when the beads are exposed to an external stimulus.

4. The implantable device of claim 1, wherein the shell comprises a first material and a second material;
wherein the first material comprises a metal-containing material or a first biodegradable material;
wherein the second material comprises a second biodegradable material;
wherein the first material is distributed in the second material; wherein the first material is configured to create pores in the second material; and
wherein the pores allow the drug to flow from within the beads to outside the beads.

5. The implantable device of claim 4, wherein the metal-containing material is configured to form pores in the shell, before or after implanting or attaching the implantable device in or on a body of a human or an animal, when the beads are exposed to an external stimulus.

6. The implantable device of claim 4, wherein the metal-containing material comprises metallic particles.

7. The implantable device of claim 6, wherein the metallic particles comprise iron-containing particles, manganese-containing particles, an iron-containing polymer or a manganese-containing polymer.

8. The implantable device of claim 4, wherein the first and second materials comprise polymers.

9. The implantable device of claim 8, wherein the first material comprises poly lactic acid (PLA) or an iron-containing polymer and the second material comprises poly E-caprolactone (PCL).

10. The implantable device of claim 1, wherein the beads further contain a polymer.

11. The implantable device of claim 1, wherein the desired flow rate of elution of the drug is substantially constant.

12. The implantable device of claim 1, wherein the desired flow rate of elution of the drug is substantially constant for a first period of time and substantially zero for a second period of time, or vice-versa.

13. The implantable device of claim 1, wherein the desired flow rate of elution of the drug is increasing or decreasing with time.

14. An implantable device comprising:
a casing, a semi-permeable membrane plug at or near a first end of the casing, a piston, beads, and an opening for release of the beads from the implantable device within a body of a human or an animal;
a sensor configured to monitor a concentration of in the body of the human or the animal;
a side wall at or near a second end of the casing, wherein the casing is substantially tubular having at least the first end of the casing and the second end of the casing, and the second end of the casing is opposite the first end of the casing;
a plate comprising open holes that allow fluid flow across the plate through the open holes and closed holes that prevent fluid flow across the plate through the closed holes, wherein the plate is located between the piston and the side wall;
a first chamber between the semi-permeable membrane plug and the piston, a second chamber between the piston and the plate, and a third chamber between the second chamber and the side wall, wherein the first chamber comprises a salt solution, the second chamber comprises the beads, and the third chamber comprises a foam;

wherein the implantable device is configured to be implanted within the body of the human or the animal during delivery of the beads into the body of the human or the animal;

wherein the beads comprise a core and a shell with the core being enclosed by the shell and the beads contain drug; and wherein the implantable device is configured to produce a desired flow rate of elution of the drug from the implantable device when the implantable device is implanted within the body of the human or the animal, and wherein the plate is configured to increase the desired flow rate of elution of the drug from the implantable device by transforming one or more of the closed holes into one or more additional open holes.

15. The implantable device of claim 14, wherein the closed holes are filled with a phase-change material.

16. The implantable device of claim 14, wherein the shell comprises a first material and a second material;

wherein the first material comprises a metal-containing material or a first biodegradable material;

wherein the second material comprises a second biodegradable material;

wherein the first material is distributed in the second material; wherein the first material is configured to create pores in the second material; and wherein the pores allow the drug to flow from within the beads to outside the beads.

17. The implantable device of claim 16, wherein the metal-containing material is configured to form pores in the shell, before or after implanting or attaching the implantable device in or on a body of a human or an animal, when the beads are exposed to an external stimulus.

18. The implantable device of claim 17, wherein the metal-containing material comprises metallic particles.

19. The implantable device of claim 18, wherein the metallic particles comprise iron-containing particles, manganese-containing particles, an iron-containing polymer or a manganese-containing polymer.

20. The implantable device of 17, wherein the metal-containing material comprises metallic particles and wherein the first and/or second materials comprise polymers.

21. The implantable device of claim 14, wherein the drug and/or the beads comprise a targeting material or a targeting molecule that binds to a certain organ, tissue, object or a specific site within the body of the human or the animal.

22. The implantable device of claim 14, wherein the shell comprises a stimuli-responsive polymer configured to break the shell, before or after implanting or attaching the implantable device in or on a body of a human or an animal, when the beads are exposed to an external stimulus.

* * * * *